United States Patent
Chang et al.

(10) Patent No.: US 12,324,879 B2
(45) Date of Patent: Jun. 10, 2025

(54) DRUG DELIVERY CONTAINER AND NEBULIZER DEVICE

(71) Applicant: HCMed Innovations Co., LTD., Taipei (TW)

(72) Inventors: Chia-Chien Chang, New Taipei (TW); Yuan-Ming Hsu, New Taipei (TW)

(73) Assignee: HCMed Innovations Co., LTD., Taipei (TW)

( * ) Notice: Subject to any disclaimer, the term of this patent is extended or adjusted under 35 U.S.C. 154(b) by 854 days.

(21) Appl. No.: 17/381,630

(22) Filed: Jul. 21, 2021

(65) Prior Publication Data

US 2022/0305216 A1 Sep. 29, 2022

(30) Foreign Application Priority Data

Mar. 25, 2021 (TW) .................. 110110743

(51) Int. Cl.
*A61M 11/00* (2006.01)
*A61M 15/00* (2006.01)

(52) U.S. Cl.
CPC ...... *A61M 11/005* (2013.01); *A61M 15/0025* (2014.02); *A61M 2205/0233* (2013.01); *A61M 2205/0294* (2013.01)

(58) Field of Classification Search
CPC .............. A61M 11/005; A61M 15/001; A61M 15/0025; A61M 15/0021; A61M 15/0026; A61M 2205/0233; A61M 2205/0294; A61M 2205/122; A61M 2205/123; A61M 2202/0468; B05B 17/0646
See application file for complete search history.

(56) References Cited

U.S. PATENT DOCUMENTS 4,976,259 A 12/1990 Higson et al.
5,435,282 A * 7/1995 Haber ............... A61M 15/0065
239/338

(Continued)

FOREIGN PATENT DOCUMENTS

CN 105636628 A 6/2016
CN 110169602 A 8/2019

(Continued)

OTHER PUBLICATIONS

Snap FitDesign Aug. 8, 2020 (Year: 2020).*
TW M603364 U description translation (Year: 2020).*
CN 111569200 A description translation (Year: 2020).*

*Primary Examiner* — Timothy A Stanis
*Assistant Examiner* — Kira B Daher
(74) *Attorney, Agent, or Firm* — Li & Cai Intellectual Property (USA) Office

(57) ABSTRACT

A drug delivery container and a nebulizer device are provided. The drug delivery container includes a body unit, a base unit, and an atomizing unit. The body unit includes a chamber element, the chamber element includes an accommodating space, an opening, and a through hole, and the accommodating space is communicated with both the opening and the through hole. The base unit includes a plurality of first conductive elements and is connected to the body unit. The atomizing unit includes a plurality of second conductive elements, and is located between the body unit and the base unit, and the second conductive elements respectively are electrically connected to the first conductive elements.

12 Claims, 7 Drawing Sheets

(56) References Cited

U.S. PATENT DOCUMENTS

| | | | |
|---|---|---|---|
| 9,339,838 B2* | 5/2016 | Moran | A61M 15/0085 |
| 10,092,924 B2* | 10/2018 | Hogan | A61M 15/0085 |
| 11,065,398 B2* | 7/2021 | Hsieh | B05B 15/18 |
| 11,882,871 B2* | 1/2024 | Lu | A24F 40/42 |
| 2005/0011514 A1* | 1/2005 | Power | A61M 11/005 |
| | | | 128/200.14 |
| 2008/0308096 A1* | 12/2008 | Borgschulte | A61M 11/005 |
| | | | 128/200.14 |
| 2009/0084867 A1* | 4/2009 | Hess | B05B 12/1409 |
| | | | 239/102.2 |
| 2010/0219263 A1* | 9/2010 | Feriani | A61M 11/005 |
| | | | 239/102.1 |
| 2016/0022927 A1 | 1/2016 | Tsai et al. | |
| 2016/0022928 A1* | 1/2016 | Cheng | A61M 15/0025 |
| | | | 128/200.14 |
| 2016/0206835 A1* | 7/2016 | Lee | A61M 15/0028 |
| 2017/0203055 A1* | 7/2017 | Chen | A61M 15/00 |
| 2019/0329281 A1* | 10/2019 | Lin | B05B 17/0623 |

FOREIGN PATENT DOCUMENTS

| | | | | |
|---|---|---|---|---|
| CN | 111569200 A | * | 8/2020 | A61M 11/005 |
| TW | 201811387 A | | 4/2018 | |
| TW | I690339 B | | 4/2020 | |
| TW | M603364 U | * | 11/2020 | |
| WO | WO 0132246 A1 | | 5/2001 | |
| WO | WO-2022079037 A1 | * | 4/2022 | A61M 11/005 |

* cited by examiner

DRUG DELIVERY CONTAINER AND NEBULIZER DEVICE

CROSS-REFERENCE TO RELATED PATENT APPLICATION

This application claims the benefit of priority to Taiwan Patent Application No. 110110743, filed on Mar. 25, 2021. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The present disclosure relates to a drug delivery container, and more particularly to a drug delivery container with an atomizing unit and a nebulizer device.

BACKGROUND OF THE DISCLOSURE

A nebulizer device is widely used in various industries, such as for purposes of cooling, humidification, disinfection, dust suppression, and medical applications. For example, when the nebulizer device is used as a medical inhaler device, a particle size of a dispensed drug must be smaller than 3 μm to 5 μm to ensure that the drug can effectively reach the lower respiratory tract and be directly absorbed by a human body, so as to improve an efficiency of the drug.

Most conventional vibrating nebulizer device uses a piezoelectric sheet to carry a nozzle plate, by the high-frequency micro-amplitude shockwave action of the piezoelectric sheet, to allow the nozzle plate to differentiate a liquid to form fine particles of vapor vector molecules upon discharge, and through the Brownian motion effect, the vapor vector molecules are mixed into the air to form medicinal water vapor, so as to provide inhalation treatment operation. However, as disclosed in Taiwan Patent No. I690339B, a detachable nebulizer device includes an atomizing seat that includes a base and has an installation chamber therein, an atomizing chamber, and a communication hole connecting the installation chamber and the atomizing chamber inside. A vibrator is disposed in the installation chamber. A container is detachably installed on the atomizing seat, and the container includes a cup with an opening, and a flexible sheet covering the opening. A piezoelectric sheet and a nozzle plate are respectively disposed on the cup and the atomizing seat. When the cup is assembled to the atomizing seat, there may not be an adequate fit between the nozzle plate and the piezoelectric sheet, resulting in poor atomizing efficiency. Moreover, some of the piezoelectric sheets of commercial nebulizers are installed on a control host. Therefore, when the piezoelectric sheet is damaged, the entire control host needs to be replaced, which causes a burden on the user.

Therefore, how to overcome the above-mentioned shortcomings by an improvement of the structural design has become one of the important issues to be solved in this industry.

SUMMARY OF THE DISCLOSURE

In response to the above-referenced technical inadequacies, the present disclosure provides a drug delivery container and a nebulizer device.

In one aspect, the present disclosure provides a drug delivery container that includes a body unit, a base unit, and an atomizing unit. The body unit includes a chamber element, the chamber element includes an accommodating space, an opening, and a through hole, and the accommodating space is communicated with both the opening and the through hole. The base unit includes a plurality of first conductive elements and is connected to the body unit. The atomizing unit includes a plurality of second conductive elements, and is located between the body unit and the base unit, and the second conductive elements are electrically connected to the first conductive elements, respectively.

In another aspect, the present disclosure provides a nebulizer device that includes a host, an atomizing chamber, and a drug delivery container. The host includes a plurality of electrical contacts. The atomizing chamber is connected to the host. The drug delivery container includes a body unit, a base unit, and an atomizing unit. The body unit is connected to the atomizing chamber. The body unit includes a chamber element, the chamber element includes an accommodating space, an opening, and a through hole, and the accommodating space is communicated with both the opening and the through hole. The base unit includes a plurality of first conductive elements and is connected to the body unit, the plurality of first conductive elements respectively correspond to the plurality of electrical contacts. The atomizing unit includes a plurality of second conductive elements, and is located between the body unit and the base unit, and the second conductive elements are electrically connected to the first conductive elements, respectively.

Therefore, by virtue of "the body unit including a chamber element, the chamber element including an accommodating space, an opening, and a through hole, and the accommodating space being communicated with both the opening and the through hole", "the base unit including a plurality of first conductive elements and being connected to the body unit", and "the atomizing unit including a plurality of second conductive elements, and being located between the body unit and the base unit, and the second conductive elements respectively being electrically connected to the first conductive elements", the drug delivery container and the nebulizer device in the present disclosure improve the practicality and the atomization efficiency. Further, when the atomizing unit is accidentally damaged or reaches the end of service life, only the drug delivery container is required to be replaced, rather than the host of the nebulizer device, thereby reducing the burden for a user.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The described embodiments may be better understood by reference to the following description and the accompanying drawings, in which:

FIG. 1 is a schematic exploded view of a drug delivery container according to a first embodiment of the present disclosure;

FIG. 2 is a schematic cross-sectional view of the drug delivery container according to the first embodiment of the present disclosure;

DETAILED DESCRIPTION OF THE EXEMPLARY EMBODIMENTS

Figure 1:
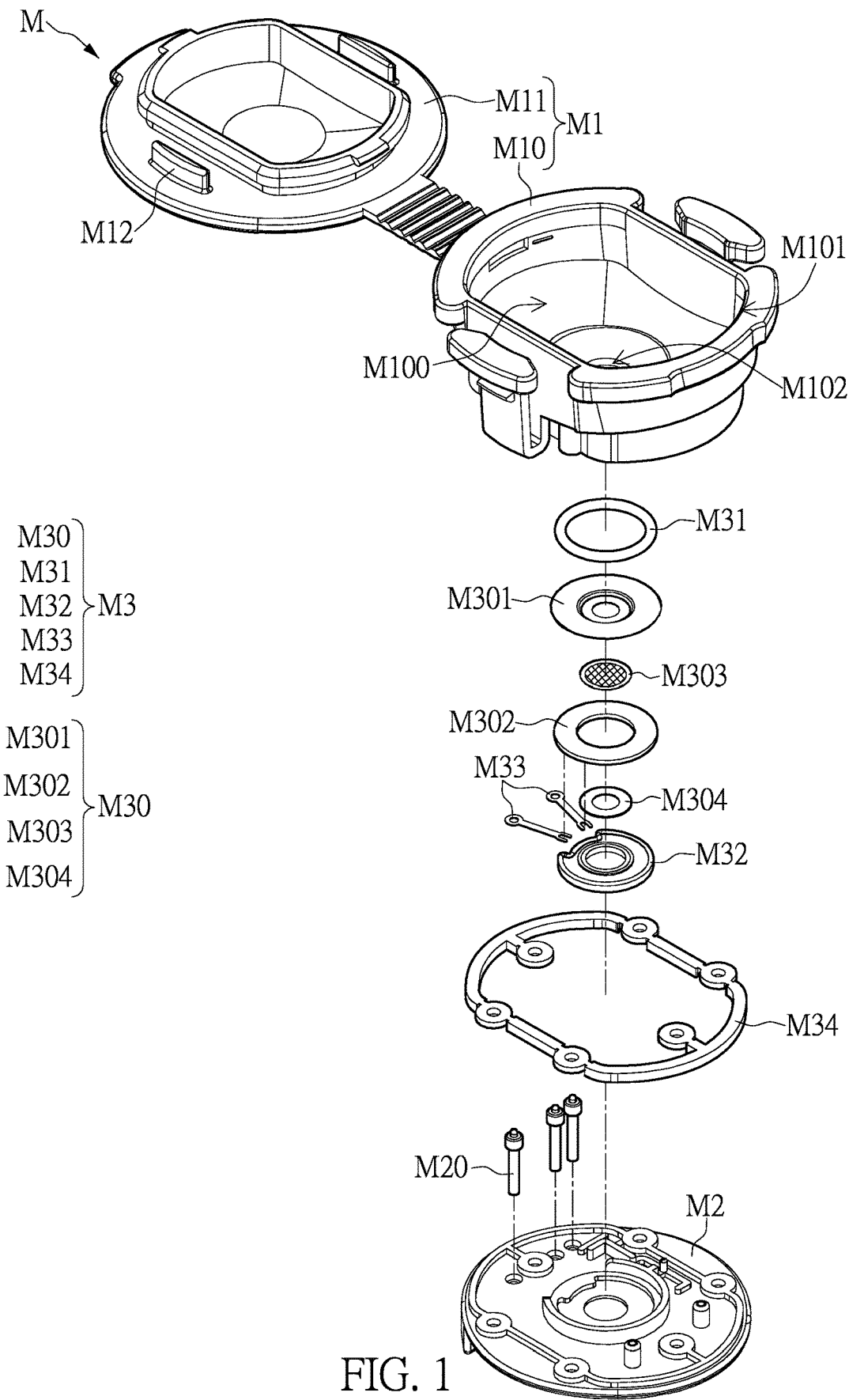

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

First Embodiment

Figure 2:
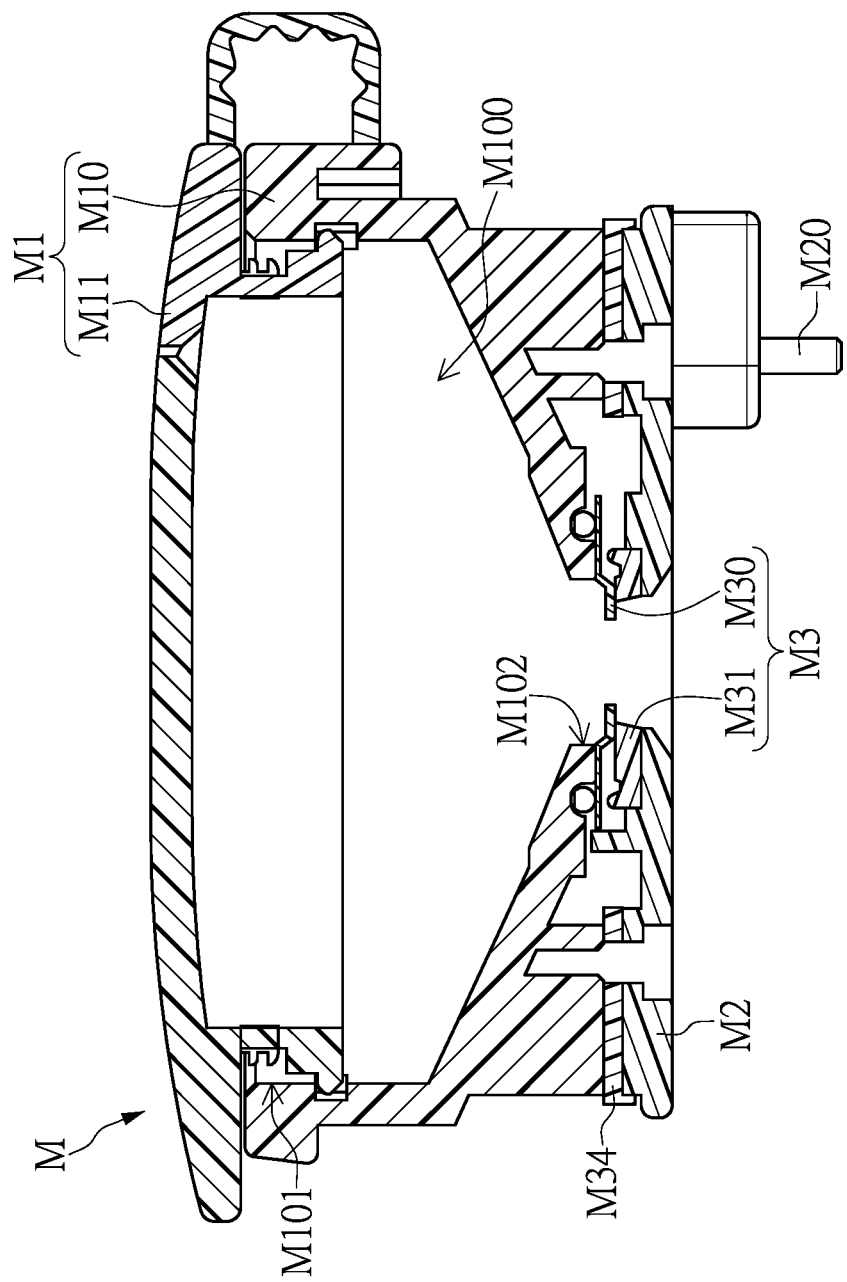
Figure 3:
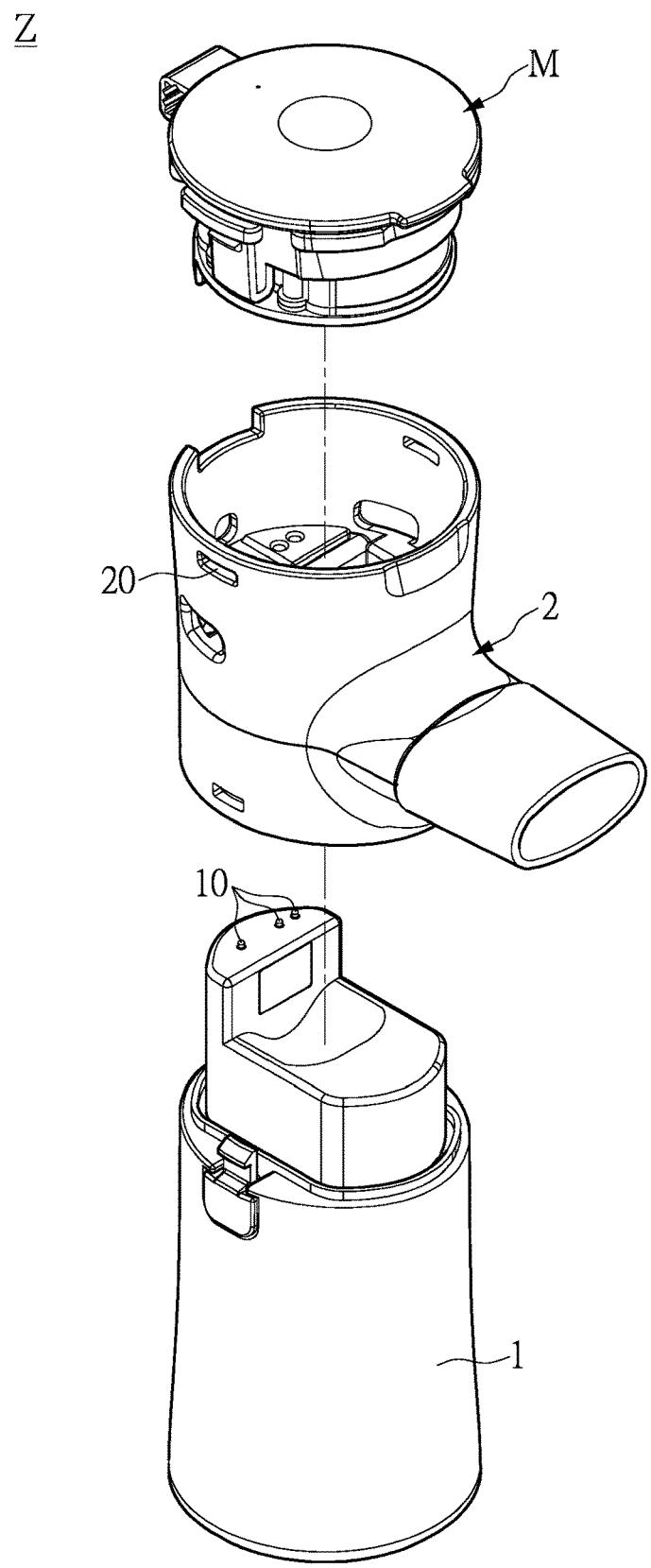
FIG. 3 is a schematic exploded view of a nebulizer device according to the first embodiment of the present disclosure.

Referring to FIG. 1 to FIG. 3, which are respectively a schematic exploded view, a schematic cross-sectional view of a drug delivery container, and a schematic exploded view of a nebulizer device according to a first embodiment of the present disclosure. Referring to FIG. 1 to FIG. 3, the first embodiment of the present disclosure provides a drug delivery container M, which includes a body unit M1, a base unit M2, and an atomization unit M3.

Firstly, referring to FIG. 1 and FIG. 2, the body unit M1 can include an accommodating space M100, and the accommodating space M100 can be used for accommodating a liquid (not shown). The liquid can be, but is not limited to, distilled water, physiological saline, artificial tears, medicinal solution, drug suspension, biological agents, etc. For instance, referring to FIG. 1, the body unit M1 can include a chamber element M10 and a cover element M11. The chamber element M10 includes an opening M101 and a through hole M102 that are disposed oppositely, and the accommodating space M100. The opening M101 and the through hole M102 are communicated with each other through the accommodating space M100, the opening M101 can be communicated with the accommodating space M100 and the outside of the chamber element M10, and the through hole M102 can be communicated with the accommodating space M100 and the outside of the chamber element M10. The cover element M11 can be a cover structure and further includes a plurality of shielding elements M12, the cover element M11 is detachably engaged to the top of the chamber element M10, and the cover element M11 can be used to shield the opening M101 or allow the opening M101 to be exposed.

Furthermore, referring to FIG. 1 and FIG. 2, the base unit M2 can be detachably engaged with the body unit M1. For instance, the base unit M2 can be a substrate structure and can be disposed at the bottom of the chamber element M10. The base unit M2 further includes a plurality of first conductive elements M20, and each of the first conductive elements M20 can be a conductive pillar, but the present disclosure is not limited thereto.

Moreover, referring to FIG. 1 and FIG. 2, the atomizing unit M3 can be located between the body unit M1 and the base unit M2. For instance, the atomizing unit M3 can include an atomizing element M30, a first waterproof element M31, and a second waterproof element M32. The atomizing element M30 includes a carry unit M301, an annular piezoelectric unit M302, a porous element M303, and a ring element M304. The porous element M303 is disposed on the carry unit M301, the annular piezoelectric unit M302 is arranged on the carry unit M301 and surrounds the porous element M303, and the ring element M304 is stacked on the porous element M303 so that the porous element M303 is exposed from the ring element M304. More specifically, the annular piezoelectric unit M302, the porous element M303, and the ring element M304 are located between the carry unit M301 and the second waterproof element M32. In addition, the porous element M303 can be a nozzle sheet or a mesh sheet, but the present disclosure is not limited thereto. The atomizing element M30 can be fixedly or detachably arranged between the first waterproof element M31 and the second waterproof element M32, the atomizing unit M3 is located between the chamber element M10 and the base unit M2, and the atomizing element M30 corresponds in position to the through hole M102 at the bottom of the chamber element M10. Specifically speaking, the atomizing unit M3 includes a plurality of the second conductive elements M33, one end of each of the second conductive elements M33 is fixed on the annular piezoelectric unit M302 of the atomizing unit M3, and another ends of the plurality of second conductive elements M33 are respectively electrically connected to the plurality of first conductive elements M20. In certain embodiments, another ends of the plurality of second conductive elements M33 are annular electrical pads, and the annular electrical pads are respectively sleeved on and electrically connected to the plurality of first conductive elements M20, but the present disclosure is not limited thereto.

In addition, when the liquid in the chamber element M10 is supplied to the atomizing element M30, with the high-frequency micro-amplitude shock wave action of the annular piezoelectric unit M302, the shock wave action drives the carry unit M301 and simultaneously actuates the porous element M303 by the carry unit M301 so that the porous element M303 can atomize the liquid to produce multiple micro mist particles.

Accordingly, the drug delivery container M provided by the present disclosure has the atomizing unit M3 arranged in the drug delivery container M through the above-mentioned technical solution, that is, the atomizing element M30 is arranged between the chamber element M10 and the base unit M2. Compared with a conventional atomizer, the drug delivery container M provided by the present disclosure has a modular structure, that is, when the atomizing element M30 is damaged, only the drug delivery container M is required to be changed, instead of replacing the host of the atomizer. Further, the stability of the atomizing element M30 in the drug delivery container M can also be improved. In addition, the drug delivery container M of the present disclosure utilizes the atomizing unit M3 that is horizontally arranged at the bottom of the chamber element M10 to effectively reduce the issue of liquid residue compared with a vertical atomization component of the conventional atomizer.

Furthermore, referring to FIG. 1 and FIG. 2, the drug delivery container M of the present disclosure can further include a third waterproof element M34, which is located between the body unit M1 and the base unit M2 and surrounds the atomizing element M30, the first waterproof element M31, and the second waterproof element M32, and the third waterproof element M34 can be a gasket structure, but the present disclosure is not limited thereto.

In addition, based on the content mentioned above, the present disclosure provides a nebulizer device Z, which includes a host 1, an atomizing chamber 2, and the drug delivery container M. The host 1 includes a plurality of electrical contacts 10. The atomizing chamber 2 is connected to the host 1. The drug delivery container M includes a body unit M1, a base unit M2, and an atomizing unit M3. The body unit M1 is connected to the atomizing chamber 2. The body unit M1 includes a chamber element M10, the chamber element M10 includes an accommodating space M100, an opening M101, and a through hole M102, and the accommodating space M100 is communicated with both the opening M101 and the through hole M102. The base unit M2 includes a plurality of first conductive elements M20 and is connected to the body unit M1, and the plurality of first conductive elements M20 respectively correspond to the plurality of electrical contacts 10. The atomizing unit M3 includes a plurality of second conductive elements M33 and is located between the body unit M1 and the base unit M2, and the plurality of second conductive elements M33 respectively are electrically connected to the plurality of first conductive elements M20.

For instance, as shown in FIG. 3, the aforementioned drug delivery container M can be applied to the nebulizer device Z. The nebulizer device Z includes the host 1, the atomizing chamber 2, and the drug delivery container M. The host can be a host of a nebulizer device and has the plurality of electrical contacts 10, and the plurality of electrical contacts 10 respectively correspond to the plurality of first conductive elements M20. The atomizing chamber 2 can also include a nozzle structure. The atomizing chamber 2 is detachably arranged on the host 1, and the drug delivery container M is detachably arranged on the atomizing chamber 2. Further, the atomizing element M30 of the drug delivery container M can be electrically connected to the host 1. More specifically, when the drug delivery container M is connected to the atomizing chamber 2 and the atomizing chamber 2 is simultaneously connected to the host 1, the plurality of first conductive elements M20 can be respectively electrically connected to the plurality of electrical contacts 10 through the atomizing chamber 2. Therefore, when a user activates the nebulizer device Z through the host 1, the liquid in the chamber element M10 can be supplied to the atomizing element M30 through the through hole M102, and then the atomizing element M30 can atomize the liquid into a plurality of micro mist particles. Next, the plurality of micro mist particles can be provided to the outside of the nebulizer device Z through the atomizing chamber 2.

However, the aforementioned description of the first embodiment is merely an example and is not meant to limit the scope of the present disclosure.

Second Embodiment

Figure 4:
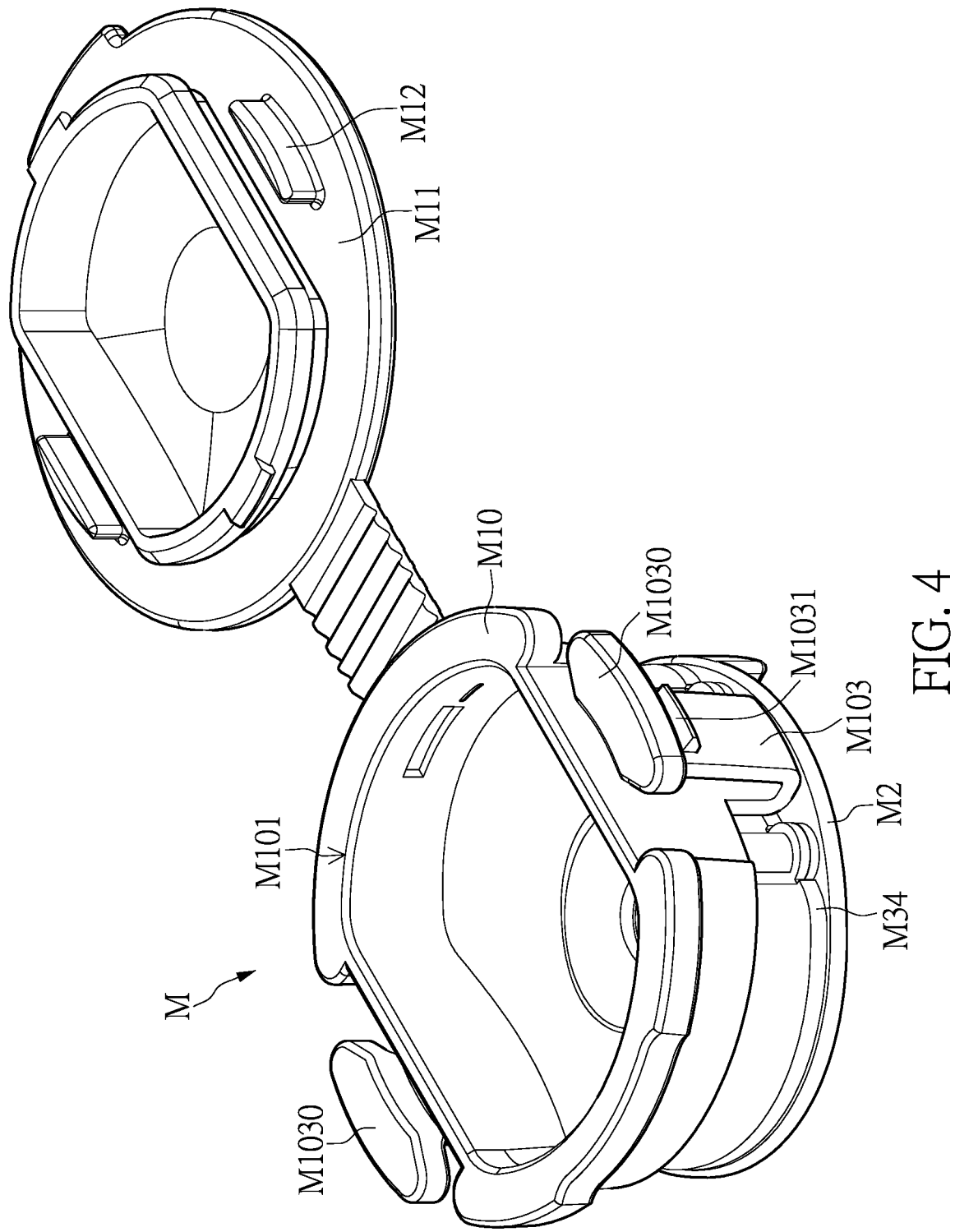
FIG. 4 is a schematic exploded view of the drug delivery container according to a second embodiment of the present disclosure.
Figure 5:
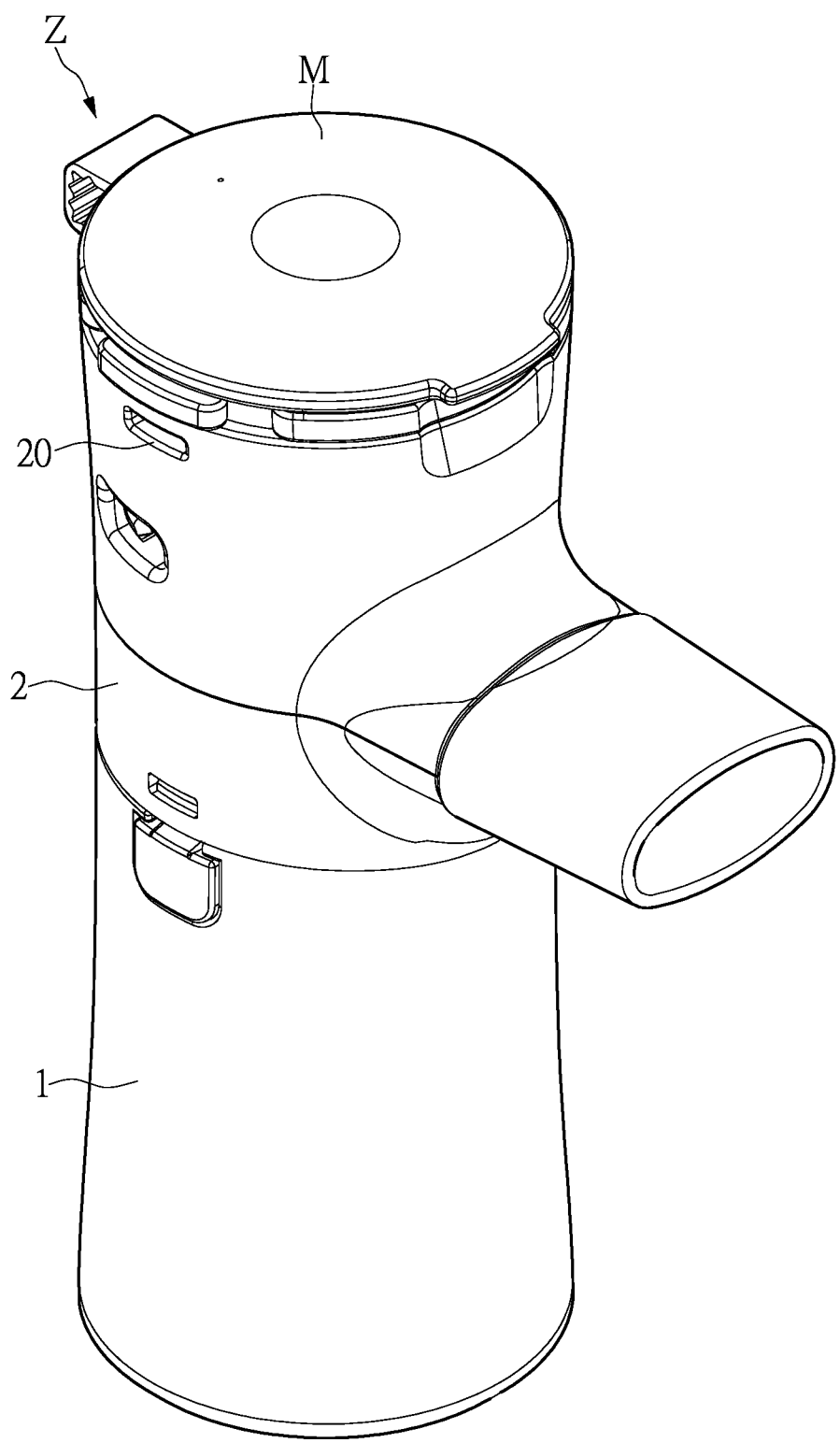
FIG. 5 is a schematic exploded view of the nebulizer device according to the second embodiment of the present disclosure.

Referring to FIG. 4 and FIG. 5, which are respectively a schematic exploded view of the drug delivery container and a schematic exploded view of the nebulizer device according to a second embodiment of the present disclosure, and are to be read in conjunction with FIG. 1 to FIG. 3. The operations of the same elements of the drug delivery container M in this embodiment are similar to those of the drug delivery container M in the first embodiment, and will not be reiterated herein. It should be noted that, in this embodiment, the side of the chamber element M10 can form a plurality of buckles M103 outwards, one end of each of the buckles M103 is connected to the chamber element M10, and each of the buckles M103 includes a limiting part M1030 and a positioning part M1031. The limiting part M1030 is located at another end of each buckle M103, the positioning part M1031 is adjacent to the limiting part M1030, and the limit part M1030 is flush with the height of the opening M101.

For instance, referring to FIG. 3 to FIG. 5, the side of the chamber element M10 can form the plurality of buckles M103 outwards, and two buckles M103 are taken as an instance in this embodiment, but the present disclosure is not limited thereto. The plurality of buckles M103 can be arranged oppositely on both sides of the chamber element M10, and the plurality of buckles M103 can have elasticity. In addition, the atomizing chamber 2 can be provided with a snap part 20 corresponding to the plurality of buckles M103, and the snap part 20 can be a slot structure, but the present disclosure is not limited thereto.

Therefore, when the drug delivery container M is assembled with the atomizing chamber 2, the positioning part M1031 on each buckle M103 is engaged with the corresponding snap part 20, and the C-shaped structure formed by the limiting part M1030, the positioning part M1031, and a part of the buckle M103 is buckled on the atomizing chamber 2, so that the drug delivery container M and the atomizing chamber 2 are firmly assembled. Further, after the drug delivery container M and the atomizing chamber 2 are assembled together, the plurality of buckles M103 can generate a pushing force toward the atomizing chamber 2, so that the drug delivery container M can be prevented from shaking. Furthermore, when the drug delivery container M is in use, the cover element M11 covers the opening M101, and the shielding elements M12 are respectively located between the limiting part M1030 and the chamber element M10, which can prevent the displacement of the limiting part M1030, thereby preventing the user from performing incorrect actions when the user operates the nebulizer device and causing the drug delivery container M to detach from the atomizing chamber 2.

Accordingly, the drug delivery container M provided by the present disclosure can enable the drug delivery container M to be firmly assembled with the atomizing chamber 2 through the above-mentioned technical solution, and can achieve the convenience of rapid disassembly or assembly.

However, the aforementioned description of the second embodiment is merely an example and is not meant to limit the scope of the present disclosure.

Third Embodiment

Figure 6:
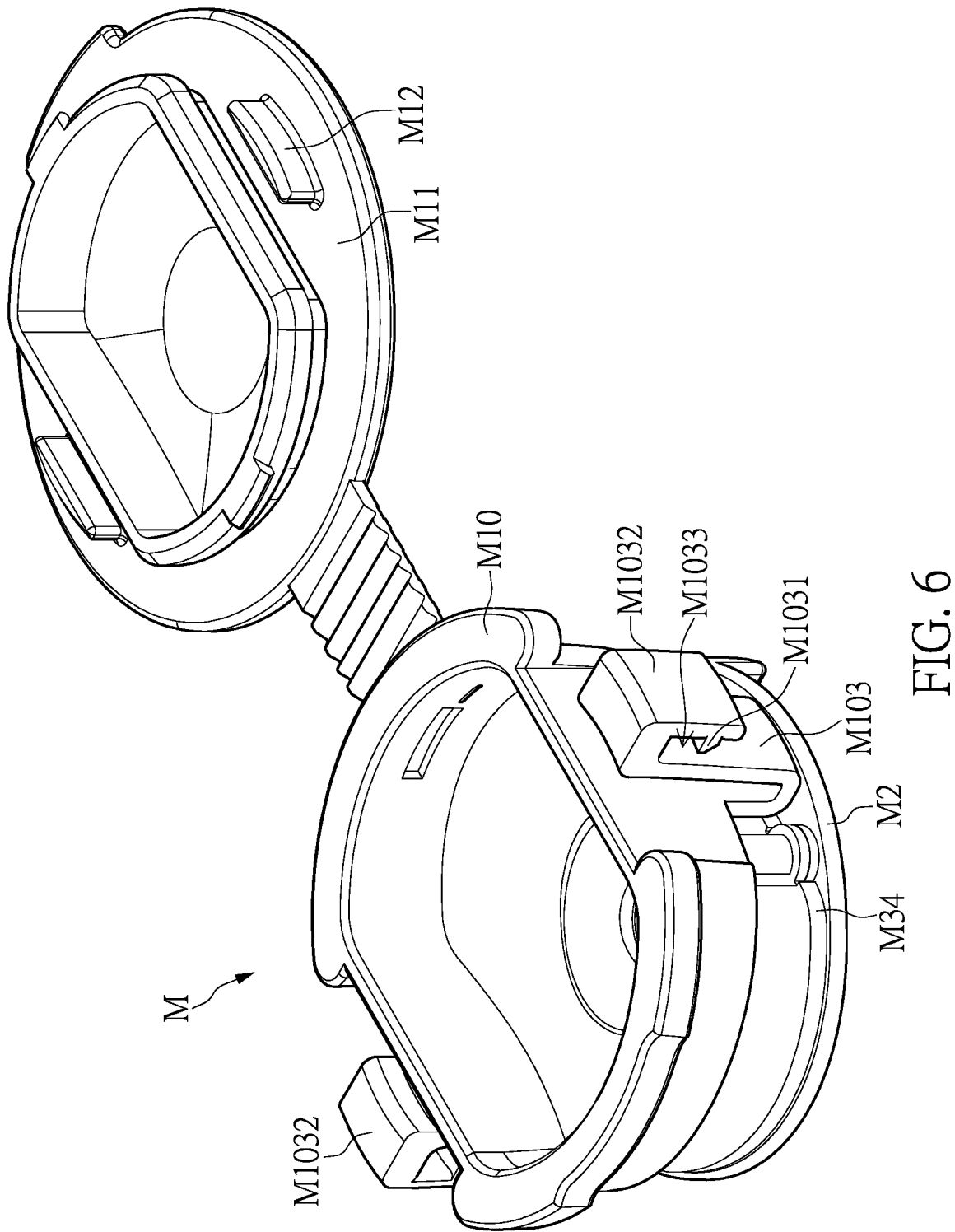
FIG. 6 is a schematic exploded view of the drug delivery container according to a third embodiment of the present disclosure.
Figure 7:
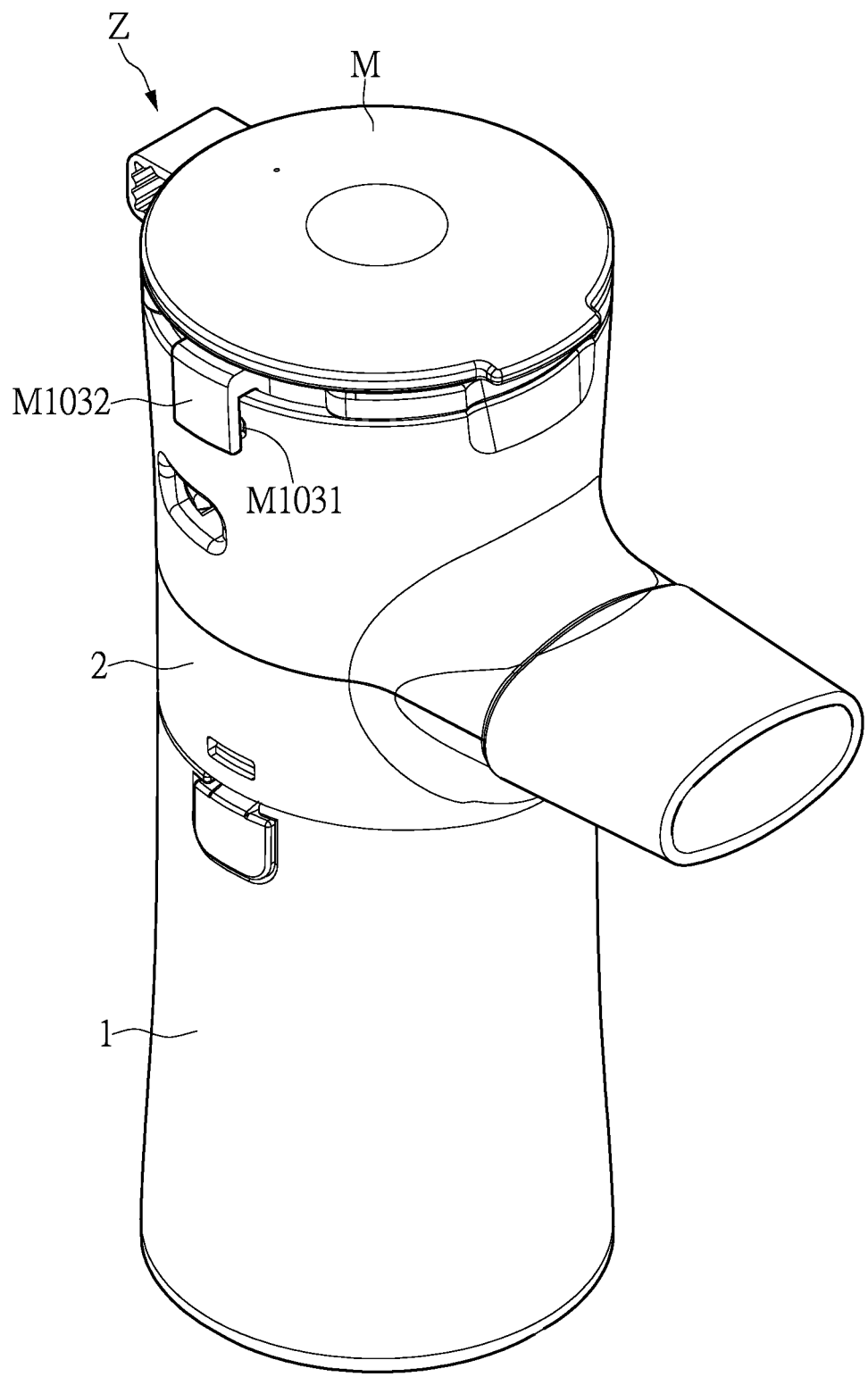
FIG. 7 is a schematic exploded view of the nebulizer device according to the third embodiment of the present disclosure.

Referring to FIG. 6 and FIG. 7, which are respectively a schematic exploded view of the drug delivery container and a schematic exploded view of the nebulizer device according to a third embodiment of the present disclosure, and are to be read in conjunction with FIG. 1 to FIG. 5. The operations of the same elements of the drug delivery container M in this embodiment are similar to those of the drug delivery container M in the aforementioned embodiments, and will not be reiterated herein. It should be noted that, in this embodiment, the side of the chamber element M10 can form a plurality of buckles M103 outwards, one end of each of the buckles M103 is connected to the chamber element M10, and each of the buckles M103 includes a fastening part M1032 and a positioning part M1031. Each of the buckles M103 is L-shaped, a retaining groove M1033 is formed between each fastening part M1032 and the main body of each buckle M103, and the positioning part M1031 is located on the fastening part M1032 and located in the retaining groove M1033.

For instance, it can be observed by comparing FIG. 4 and FIG. 6 that the difference between the drug delivery container M of this embodiment and the drug delivery container M of the second embodiment is that each of the buckles M103 of this embodiment includes the fastening part M1032 and the positioning part M1031, each of the buckles M103 is L-shaped, the retaining groove M1033 is formed between each fastening part M1032 and the main body of each buckle M103, and the positioning part M1031 is located in the retaining groove M1033.

Therefore, referring to FIG. 6 and FIG. 7, when the drug delivery container M is assembled with the atomizing chamber 2, the positioning part M1031 on each buckle M103 is engaged with the corresponding snap part 20, and the U-shaped structure formed by the fastening part M1032, the positioning part M1031, and a part of the buckle M103 is buckled on the atomizing chamber 2, so that the drug delivery container M and the atomizing chamber 2 are firmly assembled. Further, after the drug delivery container M and the atomizing chamber 2 are assembled together, the plurality of buckles M103 can generate a pushing force toward the atomizing chamber 2, so that the drug delivery container M can be prevented from shaking. Furthermore, when the drug delivery container M is in use, the cover element M11 covers the opening M101, and the shielding elements M12 are respectively located between the buckles M103 and the chamber element M10, which can prevent the displacement of the positioning part M1031, thereby preventing performing incorrect actions when the user operates the nebulizer device and causing the drug delivery container M to detach from the atomizing chamber 2.

Accordingly, the drug delivery container M provided by the present disclosure can enable the drug delivery container M to be firmly assembled with the atomizing chamber 2 through the above-mentioned technical solution, and can achieve the convenience of rapid disassembly or assembly.

However, the aforementioned description of the second embodiment is merely an example and is not meant to limit the scope of the present disclosure.

Beneficial Effects of the Embodiments

In conclusion, by virtue of "the body unit M1 including a chamber element M10, the chamber element M10 including an accommodating space M100, an opening M101, and a through hole M102, and the accommodating space M100 being communicated with both the opening M101 and the through hole M102, "the base unit M2 including a plurality of first conductive elements M20 and being connected to the body unit M1", and "the atomizing unit M3 including a plurality of second conductive elements M33, and being located between the body unit M1 and the base unit M2, and the second conductive elements M33 respectively being electrically connected to the first conductive elements M20", the drug delivery container M and the nebulizer device Z provided by the present disclosure improve the practicality and the atomization efficiency.

Further, the drug delivery container M provided by the present disclosure has the atomizing unit M3 arranged in the drug delivery container M through the above-mentioned technical solution, that is, the atomizing element M30 and the second waterproof element M32 are arranged between the chamber element M10 and the base unit M2. Compared with the conventional atomizer, the drug delivery container M provided by the present disclosure has a modular structure, that is, when the atomizing element M30 or the second waterproof element M32 is damaged, only the drug delivery container M is required to be changed, instead of replacing the host of the atomizer. Further, the stability of the atomizing element M30 and the second waterproof element M32 in the drug delivery container M can also be improved. In addition, the drug delivery container M of the present disclosure utilizes the atomizing unit M3 and the second waterproof element M32 horizontally arranged at the bottom of the chamber element M10 to effectively reduce the issue of liquid residue compared with the vertical atomization component of the conventional atomizer. Furthermore, the drug delivery container M provided by the present disclosure can enable the drug delivery container M to be firmly assembled with the atomizing chamber 2 by arranging the buckles M103 on the side of the chamber element M10, and can achieve the convenience of rapid disassembly or assembly.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A drug delivery container, comprising:
   a body unit having a tubular shell defining a longitudinal axis, including a chamber element,
   wherein the chamber element defines an accommodating space for holding a liquid dose, an opening toward a top end along the longitudinal axis, and a through hole toward a bottom end along the longitudinal axis, and the accommodating space establishes fluid communication with both the opening and the through hole from the top end to the bottom end of the body unit along the longitudinal axis;

a base unit configured to cover the bottom end of the body unit, wherein the base unit is provided with an aerosol dispensing port along and toward the bottom end of the longitudinal axis, wherein the base unit comprises a plurality of first conductive elements arranged around the aerosol dispensing port; and an atomizing unit arranged between the body unit and the base unit, configured to convert the liquid does held in the chamber element into aerosol, wherein the aerosol dispensing port expels the aerosol generated by the atomizing unit downward along the longitudinal axis, wherein the atomizing unit comprises a plurality of second conductive elements, wherein the second conductive elements are electrically connected to the first conductive elements;

wherein the plurality of first conductive elements comprise conductive pillars that protrude and are externally accessible from a bottom most surface of the base unit.

2. The drug delivery container according to claim 1, wherein the body unit includes a cover element that detachably covers the opening.

3. The drug delivery container according to claim 1, wherein the atomizing unit includes a carrying unit, an annular piezoelectric unit, a porous element, and a ring element, and wherein the porous element is disposed on the carry unit, the annular piezoelectric unit is arranged on the carry unit and surrounds the porous element, the ring element is stacked on the porous element, and the porous element is exposed from the ring element.

4. The drug delivery container according to claim 1, wherein a plurality of buckles are formed outward from a side of the chamber element, one end of each of the buckles is connected to the chamber element, and each of the buckles includes a limiting part and a positioning part, and wherein the limiting part is located at another end of each of the buckles, and the positioning part is adjacent to the limiting part.

5. The drug delivery container according to claim 1, wherein a plurality of buckles are formed outward from a side of the chamber element, one end of each of the buckles is connected to the chamber element, and each of the buckles includes a fastening part and a positioning part, the fastening part being L-shaped, a retaining groove being formed between the fastening part and the buckle, and the positioning part being located on the fastening part and in the retaining groove.

6. The drug delivery container according to claim 1, wherein one end of each of the second conductive elements is a ring-shaped electrical pad and the ring-shaped electrical pads of the second conductive elements are respectively sleeved on the first conductive elements so that the first and second conductive elements are electrically connected to each other.

7. The drug delivery container according to claim 1, further comprising a third waterproof element located between the body unit and the base unit.

8. A nebulizer device, comprising:
a control host including a plurality of upward electrical contacts;
an atomizing chamber configured to sleeve over an upper port of the host, comprising a laterally extending nozzle structure; and
a drug delivery container comprising:
a body unit configured to connect the atomizing chamber and having a tubular shell defining a longitudinal axis, including a chamber element,
wherein the chamber element defines an accommodating space for holding a liquid dose, an opening toward a top end along the longitudinal axis, and a through hole toward a bottom end along the longitudinal axis, and the accommodating space establishes is in-fluid communication with both the opening and the through hole from the top end to the bottom end of the body unit along the longitudinal axis;
a base unit configured to cover the bottom end of the body unit,
wherein the base unit is provided with an aerosol dispensing port along and toward the bottom end of the longitudinal axis,
wherein the base unit comprises a plurality of first conductive elements arranged around the aerosol dispensing port; and
an atomizing unit arranged between the body unit and the base unit, configured to convert the liquid does held in the chamber element into aerosol,
wherein the aerosol dispensing port expels the aerosol generated by the atomizing unit downward along the longitudinal axis,
wherein the atomizing unit comprises a plurality of second conductive elements,
wherein the second conductive elements are electrically connected to the first conductive elements;
wherein the plurality of first conductive elements comprise conductive pillars that protrude and are externally accessible from a bottom most surface of the base unit;
wherein the first conductive elements are electrically connected to the plurality of upward electrical contacts through the atomizing chamber.

9. The nebulizer device according to claim 8, wherein the body unit includes a cover element that detachably covers the opening.

10. The nebulizer device according to claim 8, wherein the atomizing unit includes an atomizing element, a first waterproof element, and a second waterproof element, and wherein the first waterproof element is located between the atomizing element and the through hole, and the second waterproof element is located on one side of the atomizing element opposite to the first waterproof element, wherein the atomizing element corresponds in position to the through hole.

11. The nebulizer device according to claim 8, wherein a plurality of buckles are formed outward from a side of the chamber element, one end of each of the buckles is connected to the chamber element, and each of the buckles includes a limiting part and a positioning part, and wherein the limiting part is located at another end of each of the buckles, and the positioning part is adjacent to the limiting part; wherein the chamber element is detachably engaged with the atomizing chamber by the plurality of buckles to connect with the atomizing chamber.

12. The nebulizer device according to claim 8, wherein a plurality of buckles are formed outward from a side of the chamber element, one end of each of the buckles is connected to the chamber element, and each of the buckles includes a fastening part and a positioning part, the fastening part being L-shaped, a retaining groove being formed between the fastening part and the buckle, and the positioning part being located on the fastening part and in the retaining groove; wherein the chamber element is detachably engaged with the atomizing chamber by the plurality of buckles to connect with the atomizing chamber.

\* \* \* \* \*